(12) United States Patent
Franck et al.

(10) Patent No.: US 11,534,096 B2
(45) Date of Patent: Dec. 27, 2022

(54) APPARATUS AND METHOD FOR MEASURING ELECTRODE IMPEDANCE DURING ELECTROPHYSIOLOGICAL MEASUREMENTS

(71) Applicant: KONINKLIJKE PHILIPS N.V., Eindhoven (NL)

(72) Inventors: Christoph Florian Franck, Magstadt (DE); Erwin Karl Mueller, Stuttgart (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 644 days.

(21) Appl. No.: 16/486,165

(22) PCT Filed: Feb. 20, 2018

(86) PCT No.: PCT/EP2018/054174
§ 371 (c)(1),
(2) Date: Aug. 15, 2019

(87) PCT Pub. No.: WO2018/153871
PCT Pub. Date: Aug. 30, 2018

(65) Prior Publication Data
US 2019/0387997 A1 Dec. 26, 2019

(30) Foreign Application Priority Data
Feb. 21, 2017 (EP) .................................... 17157122

(51) Int. Cl.
*A61B 5/00* (2006.01)
*A61B 5/282* (2021.01)
(Continued)

(52) U.S. Cl.
CPC ................. *A61B 5/282* (2021.01); *A61B 5/30* (2021.01); *A61B 5/316* (2021.01); *A61B 5/725* (2013.01);
(Continued)

(58) Field of Classification Search
CPC ....... A61B 5/282; A61B 5/053; A61B 5/0531; A61B 5/30; A61B 5/316; A61B 5/7225;
(Continued)

(56) References Cited

U.S. PATENT DOCUMENTS

| | | | |
|---|---|---|---|
| 6,394,953 B1 | 5/2002 | Devlin et al. | |
| 2003/0006782 A1* | 1/2003 | Shambroom | A61B 5/0531 324/614 |

(Continued)

OTHER PUBLICATIONS

International Search Report and Written Opinion, International Application No. PCT/EP2018/054174, dated May 8, 2018.
(Continued)

*Primary Examiner* — Scott M. Getzow

(57) ABSTRACT

The present disclosure is related to methods, systems and apparatus for performing electrophysiological measurements utilizing three or more electrodes attached to a patient. The system in various embodiments may include three or more electrodes attached to the patient and at least one analog-to-digital converter with external circuitry electrically coupled to the electrodes. The system may further include a microprocessor for driving the analog-to-digital conversion process, various inputs and variable frequency current outputs electrically coupled to the microprocessor for receiving signals from the electrodes and sending driven current signals to the electrodes.

12 Claims, 3 Drawing Sheets

(51) Int. Cl.
*A61B 5/30* (2021.01)
*A61B 5/316* (2021.01)
*A61B 5/259* (2021.01)
*A61B 5/276* (2021.01)

(52) U.S. Cl.
CPC ............ *A61B 5/7225* (2013.01); *A61B 5/259* (2021.01); *A61B 5/276* (2021.01); *A61B 5/6813* (2013.01); *A61B 5/7203* (2013.01); *A61B 5/7257* (2013.01); *A61B 5/742* (2013.01); *A61B 2562/04* (2013.01)

(58) Field of Classification Search
CPC ......... A61B 5/725; A61B 5/259; A61B 5/276; A61B 5/6813; A61B 5/7203; A61B 5/7257; A61B 5/742; A61B 2562/04; A61B 5/303
See application file for complete search history.

(56) References Cited

U.S. PATENT DOCUMENTS

| | | |
|---|---|---|
| 2007/0038257 A1 | 2/2007 | Gray |
| 2008/0051845 A1 | 2/2008 | Mentelos |
| 2011/0295096 A1 | 12/2011 | Bibian et al. |
| 2014/0194759 A1 | 7/2014 | Weiland et al. |
| 2014/0247058 A1* | 9/2014 | Mortara ............... A61B 5/6843 324/601 |
| 2018/0206790 A1* | 7/2018 | Oehler .................. G01R 31/64 |

OTHER PUBLICATIONS

Brigell, M. et al., "Guidelines for calibration of stimulus and recording parameters used in clinical electrophysiology of vision", Documenta Ophthalmologica, 107:185-193, 2003.

* cited by examiner

APPARATUS AND METHOD FOR MEASURING ELECTRODE IMPEDANCE DURING ELECTROPHYSIOLOGICAL MEASUREMENTS

CROSS-REFERENCE TO PRIOR APPLICATIONS

This application is the U.S. National Phase application under 35 U.S.C. § 371 of International Application No. PCT/EP2018/054174, filed on 20 Feb. 2018, which claims the benefit of European Patent Application No. 17157122.7, filed on 21 Feb. 2017. These applications are hereby incorporated by reference herein.

TECHNICAL FIELD

The present disclosure is directed generally to a system for measuring impedance in an electrode. More particularly, but not exclusively, various methods and apparatus disclosed herein relate to systems and methods for measuring the impedances in an array of electrodes used in electrophysiological measurements on human patients, such as those electrodes used in electrocardiography.

BACKGROUND OF THE INVENTION

The measurement of electrical signals transmitted in biological tissue is commonly practiced in many branches of science, and particularly medicine. Electrophysiological measurements are often taken in studying and diagnosing the human heart. Most systems used to conduct electrophysiological measurements rely on physiological electrodes that require an electrode to skin contact to operate. Commonly used examples of these electrode sensors include electroencephalography (EEG), electrocardiography (EKG), electromyography (EMG) and electrooculography (EOG), to name a few. Each of these systems requires placement of physiological electrodes in contact with the skin to conduct the corresponding electrical signals to signal processing systems. The quality of these electrical signals is highly dependent upon the quality of the connection between the electrode and the patient's body, as well as the quality of the connection between the electrode and the signal processing system itself.

Poor signal quality is often caused by high impedance electrode-skin contact, which naturally results in a poor physiological signal. In turn the poor signal is often difficult to separate from electrical noise or distortion in the system. These signal deficiencies may result in incorrect diagnoses and all the attendant dangerous that follow. Furthermore, the overall impact of poor physiological signal quality is indeterminate test results, increased medical technician time, hardware changes, and of course the expense associated with all these difficulties. Thus measuring the impedance at each electrode can help correct and rectify many signal errors in an electrophysiological measurement system and is therefore highly desirable.

The measurements or electrical activity in the heart typically involve measuring the voltage difference between a weighted sum of one set of input electrodes and a weighted sum of another set of input electrodes positioned at various points on the body. Typically, one electrode which is excluded from the group of electrodes that make up the weighted sum is an output electrode for a feedback loop which reduces common mode interference. The quality of the output electrode signal measurement is directly affected by the impedance of the skin-electrode interfaces. For example, when high impedance skin-electrode interfaces are present the signals measured usually suffer from high or increased noise and/or distortion. High impedance can be caused by improperly attached electrodes, insufficient skin preparation or aging of the electrode, for example.

Some prior art systems for measuring electrode impedance require a system to sequentially drive variable currents through each electrode in a multi-electrode system. The electrode impedance can be measured by driving an alternating current through each electrode and measuring the corresponding voltage between this electrode and another input electrode which does not have an input current of the same frequency and phase injected. This impedance measurement method is made more complex if the attached/detached and the input/output status of the electrodes can or do change during the measurement and the impedance measurement is required to function with certain electrodes detached. While many of these prior art techniques are operable, the hardware required to perform this impedance testing is typically expensive and difficult to operate.

Systems that measure electrode impedance using injected currents with one or two frequencies face several problems. Initially, not all subsets of attached electrodes may be capable of measuring impedance in these systems due to all the attached electrodes having AC current of the same frequency injected into them. In this case, the system can either not display an impedance value, or switch the frequency injected into one or more attached electrodes to a different value.

The above-described frequency switching technique has disadvantages. These systems may require additional circuitry to measure impedances accurately thereby necessitating complex internal state machines. Furthermore, these systems require calibration for each frequency that can be injected in a certain electrode, or introduce measurement error due to the circuitry having different gains at different AC voltage frequencies if only one calibration point is used.

Thus there is a need in the art for a system and method of reliably and efficiently monitoring electrode impedance in an electrophysiological measurement system while minimizing system down time and data loss.

US 2014/194759 A1 discloses a physiological data acquisition apparatus includes three or more leads, at least one AC current source, a switching mechanism structured to selectively couple the current source to selected lead pairs to inject an AC current across the selected lead pairs which produces an AC voltage across the selected lead pair, and a processing device. The processing device is structured to (i) determine an impedance across the current selected lead pair based on the AC voltage, (ii) determine whether the impedance is less than a predetermined threshold, (iii) if the impedance is less than the predetermined impedance threshold cause the current selected lead pair to be used for generating physiological parameter data, and (iv) if the impedance is not less than the threshold cause the switching mechanism to couple the at least one AC current source to a new selected pair of the leads.

US 2014/0247058 A1 discloses systems and methods for monitoring the condition of electrodes used in biological signal measurement. One method includes applying a first test signal having a first frequency to at least one of a plurality of electrodes and applying a second test signal having a second frequency to at least one of the plurality of electrodes. Both frequencies are below a frequency range associated with the biological signal. The method further includes capturing the biological signal while applying the plurality of test signals and generating an output signal that includes both the measured biological signal and the plurality of test signals. The method further includes retrieving an output amplitude for each of the plurality of test signals from the output signal and calculating an estimated impedance for each of the plurality of electrodes based on the retrieved output amplitudes of the plurality of test signals.

US 2007/0038257 A1 discloses an apparatus for assessing the electrical properties of patient electrode interfaces has a carrier signal source injecting two carrier signals comprising an AC signal with a DC offset to the electrodes. The carrier signals are out of phase. The outputs from the electrodes are formed into electrocardiographic lead signals in a pre-amplifier circuit. Signal processing circuit is coupled to the pre-amplifier circuit and provides a first signal comprising the AC carrier signal contained in an ECG lead signal and a second signal containing a DC offset signal. The first and second signals are provided to a microprocessor to obtain an output indicative of the electrical properties of electrode interfaces for the ECG lead signal.

SUMMARY OF THE INVENTION

According to aspects of the present invention, solutions to the objective described above are given in the appended independent claims. Preferred embodiments are defined in the dependent claims.

The present disclosure is related to methods, systems and apparatus for performing electrophysiological measurements utilizing three or more electrodes attached to, for example, a patient. The system in various embodiments may include three or more electrodes attached to the patient and at least one analog-to-digital converter with external circuitry electrically coupled to the electrodes. The system may further include a microprocessor for driving the analog-to-digital conversion process, various inputs and outputs electrically coupled to the microprocessor for receiving signals from the electrodes and sending driven current signals to the electrodes. The microprocessor or controller may include integral digital signal processing, and further a user interface may be employed for displaying or communicating the measured electrophysiological voltage at each electrode. In some aspects of the invention the system will include circuitry or hardware for generating at least three alternating current (AC) signals of different frequencies and injecting an AC current of one assigned frequency into each of the electrically coupled electrodes. The system of the invention may further comprise peripherals integrated into the microcontroller, such as timers, pulse width modulation outputs, or digital to analog converters for generating AC signals. Alternatively, these functions may be performed by external circuits electrically coupled to the microcontroller.

In some aspects and embodiments one input signal frequency may be assigned to each electrode, and the assignment of frequencies to the extant electrodes is chosen in a way that allows both the electrophysiological measurement and the skin-electrode impedance measurement to function if specified subsets of the electrodes are attached to the patient. In one embodiment of the invention voltages at each electrode are sampled using continuous analog-to-digital conversion of the signal measured. For the measurement of each skin-electrode impedance of an input electrode, three electrodes are utilized: 1) the input electrode (E1) whose impedance is to be measured; 2) an attached (in contact with the patient) input electrode (E2) that does not have the same frequency injected as the E1 electrode and acts as a reference, and 3) the output electrode which must be connected so it can act as a sink for the currents injected at E1 and E2.

In accordance with some aspects of the invention the microprocessor or control constructs a vector by subtracting the voltage at E2 from the one at E1; thus reducing common mode interference. The amplitude of the voltage caused by the injected current is then extracted from the signal using standard digital signal processing methods, including, but not limited to, digital filtering, discrete/fast Fourier transform, and/or the Goertzel algorithm. The impedance of a particular skin-electrode interface may, in some embodiments, be calculated from the voltage, for example by using gain/offset calibration coefficients that take into account the tolerance of the value of the injected current, the amplitude response of the external circuitry connected to the analog to digital converter (ADC) input, and the impedance of any external circuitry which appears in series with the skin-electrode impedance, which is subtracted from the measured impedance.

In various embodiments of the invention the user interface may include a low power output display such as an LED light display or an e-ink screen for displaying patient data. In some aspects of the invention an operator interface may further include a touchpad or keypad powered by the energy storage system or electrical generator to facilitate entry of patient information and system information.

In further alternative embodiments of the invention an instruction set including a method for measurement and calculation of the impedance of individual electrodes in the system is provided in storage memory.

As used herein for purposes of the present disclosure, the term "electrode" is generally used to describe various devices that establish electrical connections between a biological tissue or a patient and monitoring circuitry for the purposes of measuring electrical voltage or current changes in various biological tissues. Electrodes can be utilized in various measurement systems for performing physiological measurements including, but not limited to electroencephalography (EEG), electrocardiography (EKG), electromyography (EMG) and electrooculography (EOG).

The term "processor" or alternatively "controller" is used herein generally to describe various apparatus relating to the operation of one or more components of the system. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), programmable logic controllers and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present disclosure discussed herein. The terms "program" or "computer program" are used herein in a generic sense to refer to any type of computer code (e.g., software or microcode) that can be employed to program one or more processors or controllers.

The term "user interface" as used herein refers to an interface between a user or an operator and one or more devices that enables interaction between the user and the device(s). Examples of user interfaces that may be employed in various implementations of the present disclosure include, but are not limited to, switches, potentiometers, buttons, dials, sliders, a mouse, keyboard, keypad, various types of game controllers (e.g., joysticks), track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the disclosure, wherein.

DETAILED DESCRIPTION OF THE EMBODIMENTS

Figure 1:
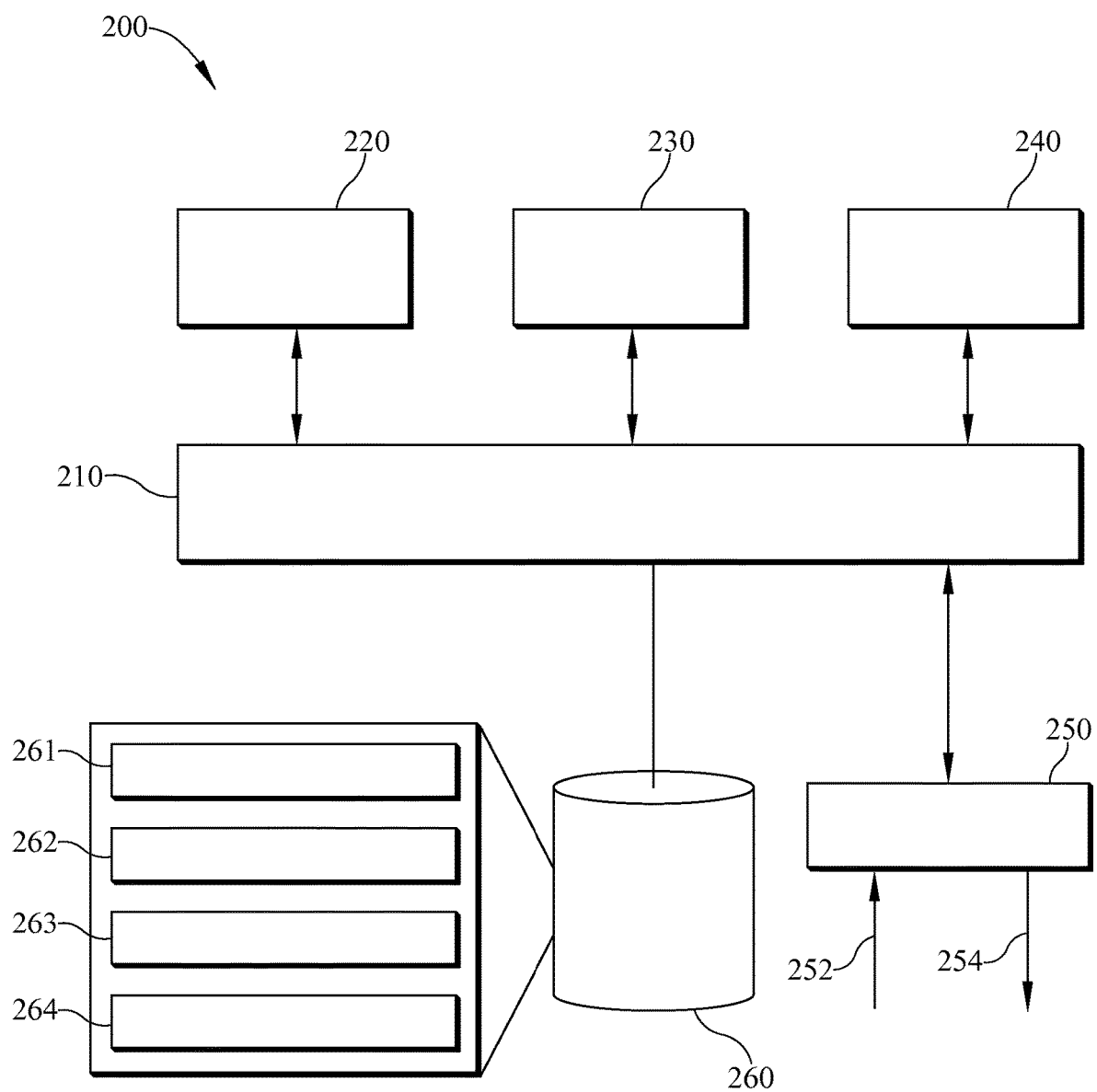
FIG. 1 graphically illustrates an exemplary hardware diagram for implementing aspects of the invention, in accordance with various embodiments.

FIG. 1 illustrates an exemplary hardware 200 diagram for implementing a system for measuring impedance of electrodes. The device 200 includes a processor 220, memory 230, user interface 240, communication interface 250, and storage 260 interconnected via one or more system buses 210. It will be understood that FIG. 1 constitutes, in some respects, an abstraction and that the actual organization of the components of the hardware 200 may be more complex than illustrated.

The processor 220 may be any hardware device capable of executing instructions stored in memory 230 or storage 260 or otherwise processing data. As such, the processor may include a microprocessor, field programmable gate array (FPGA), application-specific integrated circuit (ASIC), or other similar devices.

The memory 230 may include various memories such as, for example L1, L2, or L3 cache or system memory. As such, the memory 230 may include static random access memory (SRAM), dynamic RAM (DRAM), flash memory, read only memory (ROM), or other similar memory devices. It will be apparent that, in embodiments where the processor includes one or more ASICs (or other processing devices) that implement one or more of the functions described herein in hardware, the software described as corresponding to such functionality in other embodiments may be omitted.

The user interface 240 may include one or more devices for enabling communication with a user such as an administrator. For example, the user interface 240 may include a display, a mouse, and a keyboard for receiving user commands. In some embodiments, the user interface 240 may include a command line interface or graphical user interface that may be presented to a remote terminal via the communication interface 250.

The communication interface 250 may include one or more devices for enabling communication with other hardware devices. For example, the communication interface 250 may include a network interface card (NIC) configured to communicate according to the Ethernet protocol. Additionally, the communication interface 250 may implement a TCP/IP stack for communication according to the TCP/IP protocols. Furthermore, communication interface 250 may include a plurality of inputs 252 and outputs 254, either analog, digital, or both, of varying signal types, to enable processor 220 to receive electrical signals from a variety of sensors, for example electrodes in this instance, as well as output electrical signals, for example electrical signals at predetermined amplitudes and current levels. Inputs 252 and outputs 254 may be provided to communicate directly to processor 220 or may be send and receive digital signals to and from processor 220 respectively. Various alternative or additional hardware or configurations for the communication interface 250 will be apparent.

The storage 260 may include one or more machine-readable storage media such as read-only memory (ROM), random-access memory (RAM), magnetic disk storage media, optical storage media, flash-memory devices, or similar storage media. In various embodiments, the storage 260 may store instructions for execution by the processor 220 or data upon with the processor 220 may operate. For example, the storage 260 may store a base operating system 261 for controlling various basic operations of the hardware 200. Storage 260 may further store a plurality of instruction sets 262, 263, 264 that operate to perform necessary processor functions required to operate system 10.

It will be apparent that various information described as stored in the storage 260 may be additionally or alternatively stored in the memory 230. In this respect, the memory 230 may also be considered to constitute a "storage device" and the storage 260 may be considered a "memory." Various other arrangements will be apparent. Further, the memory 230 and storage 260 may both be considered to be "non-transitory machine-readable media." As used herein, the term "non-transitory" will be understood to exclude transitory signals but to include all forms of storage, including both volatile and non-volatile memories.

While the hardware 200 is shown as including one of each described component, the various components may be duplicated in various embodiments. For example, the processor 220 may include multiple microprocessors that are configured to independently execute the methods described herein or are configured to perform steps or subroutines of the methods described herein such that the multiple processors cooperate to achieve the functionality described herein. Further, where the device 200 is implemented in a cloud computing system, the various hardware components may belong to separate physical systems. For example, the processor 220 may include a first processor in a first server and a second processor in a second server.

Figure 2:
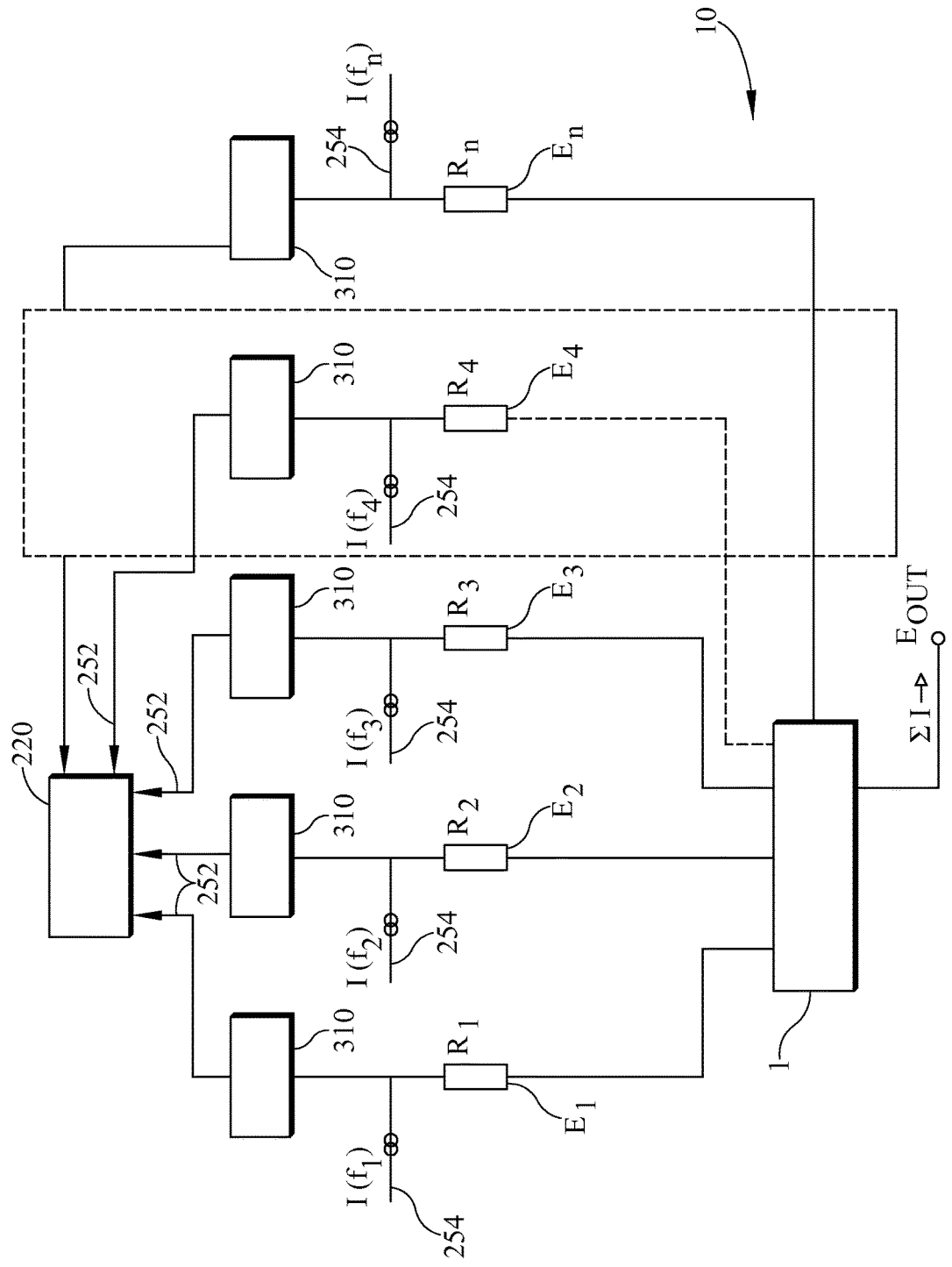
FIG. 2 depicts an exemplary electrical diagram in accordance with various embodiments of the invention.
Figure 3:
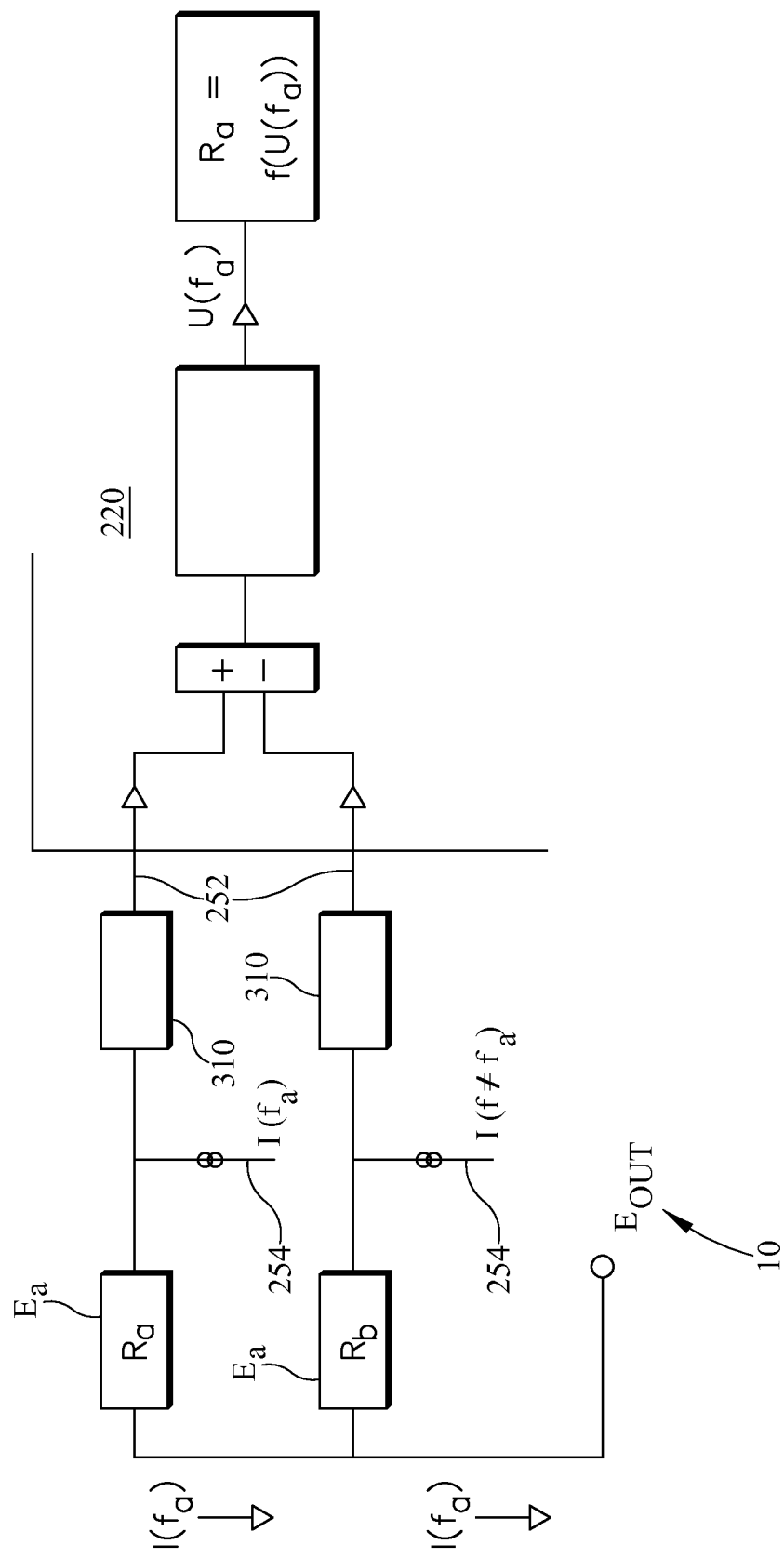
FIG. 3 depicts an exemplary electrical diagram in accordance with various embodiments of the invention.

Referring now to FIGS. 2 and 3, and in accordance with various embodiments of the invention, the system 10 for measuring skin to electrode impedance of a patient 1 may include three or more electrodes E1, E2, E3, ... En, attached to a patient, each of said electrodes En having an electrode to skin impedance, denoted in FIG. 2 as R1-Rn. Each electrode En is electrically coupled to an analog-to-digital converter 310 that provides an input 252 to processor 220, thereby providing processor 220 with a digital representation of a voltage at En. In addition to driving the analog-to-digital conversion and digital signal processing functions of the invention, controller 220 provides outputs 254 to user interface 240, thereby displaying or communicating the measured electrophysiological voltage at any electrode En.

In accordance with some embodiments of the invention controller 220 further comprises a plurality of outputs 254, which can comprise many different known circuits or hardware, for generating at least three AC current signals, denoted in FIG. 2 as I(f1)-I(fn) of different frequencies. These current signals I(fn) are then electrically coupled or injected into each of the electrodes, by supplying one assigned frequency I(fn) to each electrode. In accordance with some embodiments various peripheral circuitry may be integrated into the processor 220, for example timers, pulse width modulation outputs 254, or digital to analog converters that may be used to generate the AC current signals. Alternatively, in some embodiments these signal generating functions may be produced or provided by external circuitry and driven by instructions or outputs 252 from processor 220.

In some embodiments the impedance measurement Rn of one electrode-skin interface requires three electrodes to operate. First electrode E1, whose impedance is being measured, is provided an AC current I(f1) at a predetermined frequency f1. A second electrode E2 is provided an AC current I(f2) at a predetermined second frequency f2 in which f2≠f1, that is to say E2 is not supplied with an AC current of the same frequency as E1. A third electrode Eout acts as a sink for all the currents I(fn) injected into the other electrodes, and thus serves as the output electrode for the physiological measurement being conducted.

In this embodiment of the invention the voltages at electrode E1 which is caused by the injected currents I(f1) in conjunction with the skin-electrode impedance R1, is measured in system 10 by continuous sampling and analog-to-digital conversion of the voltages at E1 and E2 by AD converters 310. Processor 220 then subtracts the two voltages measured at E1 and E2 to reduce common mode interference. Processor 220 then subsequently extracts the amplitude of the voltage at E1 caused by the injected AC current output with known methods of digital signal processing. In some aspects and embodiments of the invention processor 220 processes the measured voltage signals by techniques including, but not limited to, a combination of digital filtering, discrete Fourier transform, fast Fourier transform, and/or the Goertzel algorithm. Once the amplitude of the voltage at electrode E1 is known, the impedance R1 of the skin-electrode interface is then derived from the voltage at E1, for example by using gain/offset calibration coefficients in accordance with known methods for calculating impedances.

In some embodiments of the invention as used in an exemplary ECG (electrocardiogram), system 10 may be employed by utilizing three electrodes typically positioned on the right arm (RA), left arm (LA), and left leg (LL) of a patient. As is known in the art, the ECG electrode E positions RA, LA, RL, and LL are not necessarily on a patient's limbs per se, but are conventionally located on the right shoulder (RA), left shoulder (LA), right lower abdomen (RL) and left lower abdomen (LL). System 10, and specifically processor 220 is then capable of measuring capable of measuring one of three signal vectors: either vector I between RA-LA electrodes, vector II between RA-LL electrodes or vector III between LA-LL electrodes. Furthermore, processor 220 then selects whichever electrode is not used in the vector measurement, (the unused electrode) as an output electrode. By assigning one of three different frequencies f1, f2, f3 to each of the three electrodes (e.g. f1/RA, f2/LA, f3/LL), it is assured that for each of the two input electrodes selected there is another input electrode which does not have the same frequency injected, and the electrode-skin impedance measurement described in detail herein above utilizing three electrodes per skin-electrode interface can be accomplished for each of the two input electrodes.

In some embodiments and aspects of the invention, system 10 can be employed as an ECG system utilizing four electrodes (RA, LA, LL and Right Leg-RL), in which RL is always selected to be used as the output electrode when it is connected to the patient 1. In this embodiment the system 10 is required to measure at least one ECG vector between two electrodes RA, LA, LL if any three out of the four electrodes are connected. Furthermore, additional ECG vectors become available to be used if all four electrodes are connected. By assigning one of the three frequencies f1, f2, f3 to RA, LA, LL and assigning either f1, f2 or f3 to RL (e.g. f1/RA, f2/LA, f3/LL, f1/RL), the system 10 can then measure the ECG wave as required for patient diagnosis, and further measure the impedance Rn of each connected input electrode RA, LA, LL if any subset of three electrodes is electrically connected to the patient.

Referring again to FIGS. 2 and 3, in a further embodiment system 10 can be employed as an ECG measurement system utilizing five or more electrodes (RA, LA, LL, RL, and, for example, chest electrodes V1, V2, ... Vn). Again, in multiple electrode ECG systems such as this one the RL electrode is always used as an output electrode if it is connected to the patient 1, and the system 10 is required to measure at least one ECG vector if any three out of the four electrodes RA, LA, LL, RL are connected to the patient 1. In this embodiment, the invention assigns one of the three frequencies f1, f2, f3 to the RA, LA, LL electrodes respectively, and assigns one of f1, f2 or f3 to the RL, V1, V2 ... Vn electrodes. (e.g. f1/RA, f2/LA, f3/LL, f1/RL, f2/V1, f1/V2 ... ). By using this frequency assignment, it is possible for system 10 to measure the ECG wave as required for patient 1 diagnosis and further measure the impedance of each connected input electrode if any subset of three electrodes out of RA/LA/LL/RL is connected.

In yet other aspects and embodiments, system 10 consists of an EEG system utilizing four or more electrodes En, in which the output electrode Eout does not change and the impedance measurement is required to work if at least two input electrodes are connected. In this embodiment of the instant invention, the impedance Rn measurement and determination technique uses as many frequencies as there are possible input electrodes En, whereby a unique individual signal frequency fn is assigned to each input electrode En. The assignment of a unique frequency fn assures that if at least two input electrodes E1, E2 and the output electrode Eout or E3 are connected to the patient 1, the skin-electrode interface impedance can be measured using the three-electrode method described herein above.

In various aspects of the invention it should be noted that the techniques and systems 10 disclosed herein, while discussing exemplary systems for ECG monitoring and diagnoses, are equally applicable to other electrophysiological measurements, including but not limited to electroencephalography (EEG), electrocardiography (EKG), electromyography (EMG) and electrooculography (EOG). In operation, the invention can be employed to detect electrode to skin impedance Rn by measuring the current(s) that an electrophysiological measurement device injects into the electrode En connections. If there are more than two different frequencies of injected currents, and the assignment of these frequencies to electrodes En is chosen in a way that respects specified subsets of electrodes and does not change during the measurement, it is possible to detect all the required impedances Rn in the system 10 without the necessity of frequency switching and all the attendant difficulties and expense that known technique entails.

In some aspects of the invention system 10 may employ the following method for measuring the impedance R1 of an electrode E1-skin interface of a patient 1. Initially system 10 processor 220 provides a plurality of signal outputs I(f1)-I(fn) (254) to a plurality of electrodes En that are placed in contact with the skin of a patient 1. In an exemplary but non-limiting three electrode system the frequency of the alternating current output injected into a first electrode E1 is different from the alternating current output injected into a second electrode E2. In such a system a third electrode E3 is selected as a current sink and output electrode. Each attached electrode En is electrically coupled to an analog to digital converter ADC, 310, which in turn supplies a digital output to an input 252 of processor 220 that is indicative of a voltage measured at the skin-electrode interface. This resultant voltage at E1 and E2 may then be subtracted to reduce common mode interference, and then the impedance at E1 may be calculated by applying selected signal processing to the voltage at E1, to derive the amplitude of the E1 voltage. Non-limiting examples of signal processing techniques that may be employed include digital filtering, discrete Fourier Transforms (DFT), Fast Fourier Transforms (FFT) and Goertzel algorithms. Once the E1 voltage amplitude is derived, impedance at the E1 skin-electrode interface is then calculated by applying the system offset calibration and gain coefficients to the derived voltage.

While various inventive embodiments have been described and illustrated in this specification, those of ordinary skill in the art may discern a variety of other systems or structures for performing the functions and/or obtaining the results and advantages described herein. Each of these variations and modifications is deemed to be within the scope of the inventive embodiments described herein. One of ordinary skill in the art will readily appreciate that all parameters, dimensions, materials, and configurations described herein are meant to be exemplary of the invention, and that the actual parameters, dimensions, materials, and configurations will depend upon the specific application or applications of the invention. Furthermore, those skilled in the art will recognize, or be able to ascertain using no more than routine experimentation, many equivalents to the specific inventive embodiments described herein. Accordingly, it is understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described in this specification. Any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

In an aspect, a system for measuring the impedance of an electrode-skin interface of a patient is provided, said system comprising: at least three electrodes arranged to be electrically coupled to said patient at a plurality of points, each of said at least three electrodes electrically coupled to an analog to digital converter; a processor having a plurality of inputs electrically coupled to said analog to digital converters for measuring a signal representative of voltage at each of said electrodes; and a plurality of alternating current outputs configured to supply each of said three electrodes with a unique frequency current signal, wherein the alternating current outputs are configured to supply a first and a second of said three electrodes with current and the third of said electrodes is designated as an output electrode acting as a sink for currents input into the first and second electrode.

In a further aspect, a system for measuring the impedance if an electrode-skin interface of a patient is provided, said system comprising: a plurality of electrodes electrically coupled to said patient at a plurality of points, each of said plurality of electrodes electrically coupled to an analog to digital converter; a processor having electrically coupled to said analog to digital converter of each electrode, for measuring a signal representative of voltage at each of said electrodes and; a plurality of alternating current outputs arranged to supply currents at different frequencies to said plurality of electrodes.

The invention claimed is:

1. A system for measuring the impedance of an electrode-skin interface of a patient, said system comprising:
   at least three electrodes arranged to be electrically coupled to said patient at a plurality of points, each of said at least three electrodes electrically coupled to an analog to digital converter;
   a processor having a plurality of inputs electrically coupled to said analog to digital converters for measuring a signal representative of voltage at each of said electrodes; and
   a plurality of alternating current outputs configured to supply each of said at least three electrodes with a unique frequency current signal, wherein
   for any subset of the at least three electrodes, the alternating current outputs are configured to supply a first and a second of said three electrodes with current and a third of said electrodes is designated as an output electrode acting as a sink for currents input into the first and second electrode.

2. The system of claim 1, comprising:
   a digital signal processing system for calculating a voltage at an electrode.

3. The system of claim 2, wherein said digital signal processing system is configured to determine a skin-electrode impedance based upon the voltage at the first electrode.

4. The system of claim 2, wherein said digital signal processing system is arranged to subtract the voltage at the second electrode from the voltage at the first electrode.

5. The system of claim 2, wherein said digital signal processing system is arranged to perform digital filtering.

6. The system of claim 2, wherein said digital signal processing system is arranged to apply a discrete Fourier transform.

7. The system of claim 2, wherein said digital signal processing system is arranged to apply a fast Fourier transform.

8. The system of claim 2, wherein said digital signal processing system is arranged to apply a Goertzel algorithm.

9. The system of claim 1, wherein said at least three electrodes comprise at least three electrodes for electrocardiography.

10. The system of claim 9, wherein said third electrode designated as an output electrode arranged to be secured to the skin at an RL position of said patient.

11. The system of claim 1, comprising:
    a fourth electrode acting as an input electrode for an ECG system.

12. A method of determining skin-electrode impedance in an electrophysiological measurement system having at least three electrodes securable to skin of a patient, said method comprising the steps of:
    electrically coupling said electrodes to said patient at different points;
    electrically coupling each of said electrodes to an analog to digital converter;
    electrically coupling said analog to digital converters to a processor having at least as many inputs as there are electrodes, for measuring signals representative of voltage at each of said at least three electrodes;
    for any subset of the at least three electrodes, supplying alternating current output signals at uniquely assigned frequencies to said at least three electrodes;
    assigning a third electrode as an output electrode acting as a sink for currents input into a first and a second of said three electrodes; and
    determining the skin-electrode impedance at one of the first and the second electrodes by measuring a voltage at that electrode for a predetermined current signal.

* * * * *